US005208788A

United States Patent [19]

Dancer et al.

[11] Patent Number: 5,208,788

[45] Date of Patent: May 4, 1993

[54] DISCHARGE CIRCUIT, AND USE THEREOF IN A METHOD AND IN APPARATUS FOR DETECTING AND CORRECTING THE POSITIONS OF ELECTRODES, IN PARTICULAR AS USED IN APPARATUSES FOR GENERATING PRESSURE WAVES

[75] Inventors: Paul Dancer, Saint Etienne; Maurice Bourlion, Saint Chamond, both of France

[73] Assignee: Technomed International, Paris, France

[21] Appl. No.: 729,710

[22] Filed: Jul. 15, 1991

[30] Foreign Application Priority Data

Jul. 16, 1990 [FR] France ............................... 90 09052

[51] Int. Cl.[5] ......................... G01V 1/00; A61B 17/22

[52] U.S. Cl. ................................ 367/147; 128/24 EL

[58] Field of Search ................... 367/147; 128/24 EL, 128/24 A, 24 AA, 662.03; 181/113

[56] References Cited

U.S. PATENT DOCUMENTS

| | | | |
|---|---|---|---|
| 2,559,227 | 7/1951 | Rieber | 367/147 |
| 4,868,791 | 9/1989 | Cathignol et al. | 367/147 |

*Primary Examiner*—Brian S. Steinberger

*Attorney, Agent, or Firm*—Cohen, Pontani, Lieberman, Pavane

[57] ABSTRACT

The invention relates to an electrical discharge circuit between two electrodes. The circuit includes switch means connected in parallel between the electrodes and constituting a switch that is closed for low frequency currents and that is open for high frequency currents. The discharge circuit may be used to detect and correct the position of an electrode at will, in manner that is simple, reliable, cheap, and suitable for being automated.

13 Claims, 2 Drawing Sheets

Invention

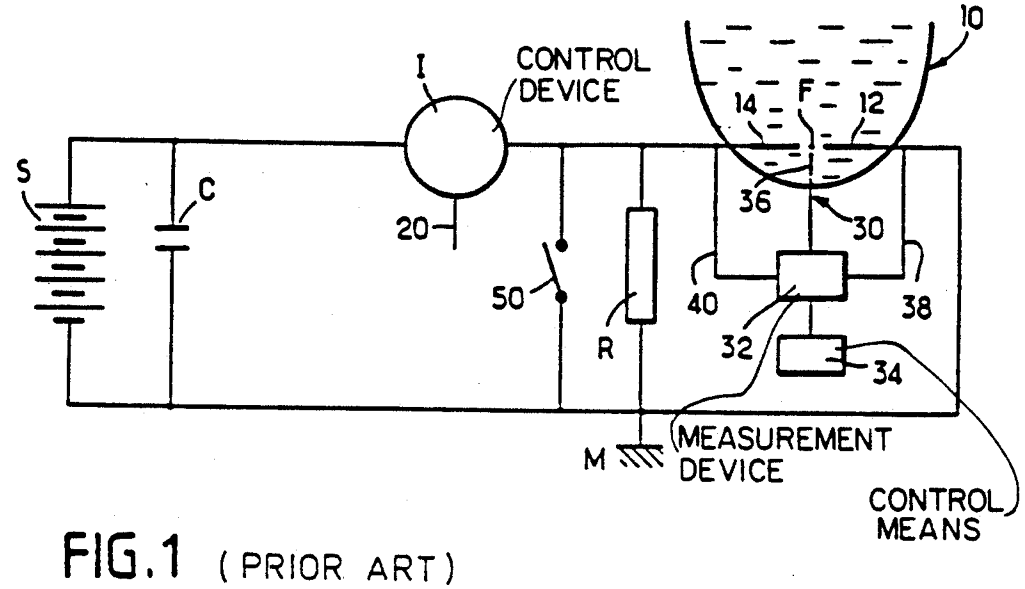
FIG.1 (PRIOR ART)
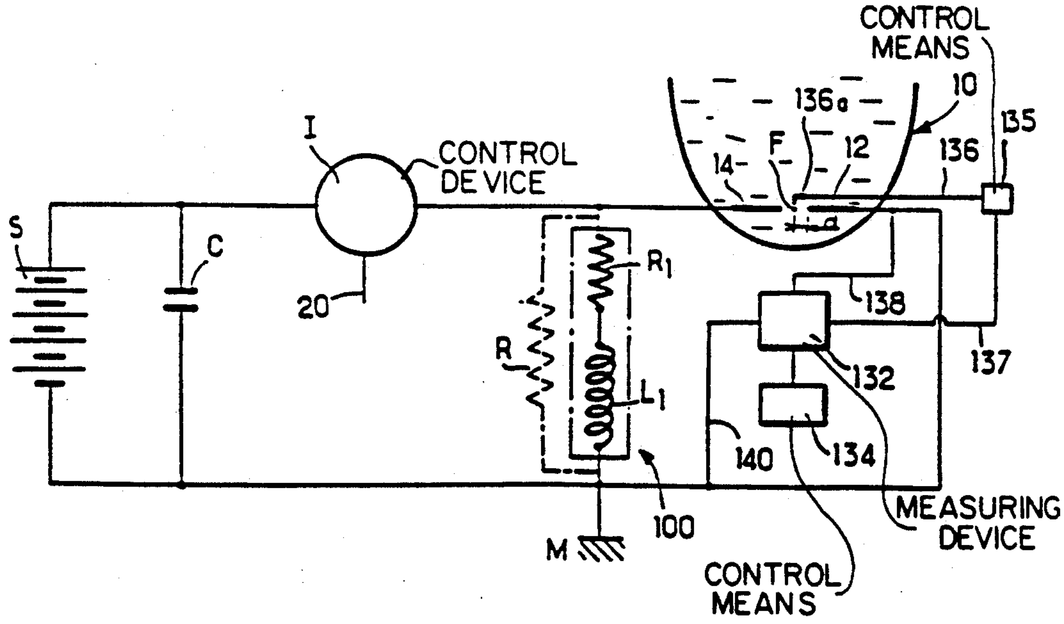
FIG.2 Invention

DISCHARGE CIRCUIT, AND USE THEREOF IN A METHOD AND IN APPARATUS FOR DETECTING AND CORRECTING THE POSITIONS OF ELECTRODES, IN PARTICULAR AS USED IN APPARATUSES FOR GENERATING PRESSURE WAVES

The invention relates essentially to an improved discharge circuit, and to the use thereof in a method and apparatus for detecting and correcting the positions of electrodes, in particular as used in apparatuses for generating pressure waves, and in which the electrodes are immersed in a liquid.

BACKGROUND OF THE INVENTION

The present Assignee's U.S. Pat. No. 4,868,791 describes a method and an apparatus for detecting and correcting an electrode, in particular for use in shock wave generator apparatuses, the method and apparatus making use of a feeler finger that is brought to the focal point, and constituted, in particular, by the rod of an actuator. As can be seen from FIG. 4 of U.S. Pat. No. 4,868,791, a resistance is connected in parallel between the electrodes, said resistance usually being about 10 kilohms. A switch is also provided to ground the positive electrode during a detection test in combination with the feeler finger.

It is necessary for the resistance of about 10 kilohms to be present for the purpose of fixing the potential between the electrodes, for safety reasons. During an electrical discharge, it will be understood that as much current as possible must pass between the electrodes in order to obtain maximum effectiveness of the shock wave, thereby implying that the resistance must be relatively high in order to prevent it absorbing too much current.

Unfortunately, this conflicts with correcting the centering of the electrodes where it is desirable to detect changes in resistance that are much less than about 10 kilohms when the electrode is very close to the feeler finger. In that prior patent of the Assignee, the grounding switch used is an expensive component is that bulky and difficult to implement since it is a switch that must be capable of isolating voltages lying in the range 10 kV to 20 kV, while also being capable of being driven by an external source, e.g. compressed air. In addition, like any mechanical member, it suffers from problems of reliability over a period of time and requires maintenance.

An object of the present invention is thus to solve the novel technical problem consisting in providing an electrical discharge circuit for providing a discharge between two discharge electrodes that are immersed in a liquid, the circuit being capable of fixing the low frequency potential of the positive electrode.

Another object of the present invention is to solve the novel technical problem consisting in providing an electrical discharge circuit for providing a discharge between two discharge electrodes, immersed in a liquid, the circuit making it possible to detect and correct electrode positions in a manner that is simpler, more reliable, and less expensive, thus being suitable for use on an industrial scale.

Another object of the present invention is to solve the novel technical problem consisting in providing a discharge circuit suitable for use in apparatuses for generating pressure waves, as used in therapeutic treatments such as lithotrity, osteotrity (bone treatment), or treatment of tissue, in particular tumors, with the discharge electrodes being immersed in a liquid.

These technical problems are solved for the first time by the present invention in a manner that is satisfactory, reliable, cheap, and usable on an industrial scale.

SUMMARY OF THE INVENTION

Thus, in a first aspect, the present invention provides an electrical discharge circuit for providing a discharge between two discharge electrodes, comprising a discharge circuit proper for providing a discharge between said electrodes immersed in a liquid by intermittently connecting a source of high tension current to each of said two electrodes, wherein the circuit further includes switch means connected in parallel between the electrodes, said switch means constituting a switch that is closed for low frequency currents and a switch that is open for high frequency currents.

In a preferred embodiment of this circuit, the above-specified switch means comprise a choke.

In an advantageous variant embodiment, the choke has an impedance that is very large compared with the impedance of the electrodes at the moment of discharge, and preferably, the impedance of the choke is at least 100 times greater, and better at least 500 times greater, and better still at least 1,000 times greater than the impedance between the electrodes at the moment of discharge.

In a variant embodiment of the device of the invention, a resistance may also be provided in parallel with the above-mentioned switch means comprising a choke.

In a second aspect, the present invention also provides the use of the above-specified electrical discharge circuit in apparatus for detecting and correcting the positions of two electrodes.

In a third aspect, the present invention also provides a method of detecting and correcting the position of an electrode, in particular for use in pressure wave generator apparatuses, such electrodes needing to be disposed at a predetermined distance symmetrically about a point accurately determined in three dimensions at which an electrical discharge is to be generated between the electrodes, said point being called the "focal" point, and said electrodes being immersed in a liquid, the method comprising the following steps:

- bringing a detector means capable of detecting the presence of an electrode at a determined point in three dimensions, which point is referred to as the "detection" point and is situated either at the focal point or else on the displacement path of the electrodes;
- advancing one of the electrodes until it comes into contact with said detector means while disposed at the detection point;
- detecting the presence of the electrode at said detection point;
- withdrawing the electrode to position the electrode at its predetermined distance;
- preforming the same procedure with the other electrode(s); and
- withdrawing the detector means from said detection point;
- wherein switch means are provided connected in parallel between the electrodes to form a switch that is closed for low frequency currents and to form a switch that is open for high frequency currents, with DC being applied permanently to the detector means and with variation in the resistance between the detector means and the electrode being detected.

Preferably, the switch means comprise a choke.

The present invention also relates to an apparatus for detecting and correcting electrode position, particularly in pressure wave generator apparatuses, the apparatus comprising displaceable detector means suitable for being brought to and for being withdrawn from a predetermined point in three dimensions called the "detection" point and situated either at the focal point or else on the path along which the electrodes move, for the purpose of detecting the presence of an electrode at the detection point, a device for measuring electrical resistance between the detector means and the electrode, and an item indicating changes in said resistance, with the electrodes being immersed in a liquid, the apparatus including switch means connected in parallel between the electrodes to form a closed switch for low frequency current and to form an open switch for high frequency current.

The switch means preferably comprise a choke.

It will be understood that with the present invention, by using a choke connected in parallel between the electrodes, the low frequency potential of the positive electrode is fixed, thereby making it possible to eliminate the positive electrode switch for grounding the positive electrode momentarily, as has been used in the past in patent U.S. Pat. No. 4,868,791, the choke acting as a switch at high frequency like a switch that is open. It is thus possible to detect and correct the positions of the electrodes in a manner which is particularly simple and cheap while improving the reliability of pressure wave generator apparatuses such as lithotritors, osteotritors, and apparatuses for treating tissue, in particular tumors.

The invention makes it possible to perform automatic centering in water by performing an electrical measurement of contact between and electrode and a detector means such as a feeler finger. The invention also simplifies the discharge circuit, increases its reliability, and decreases its cost by using an electronic component that does not need maintenance. The invention makes it possible to eliminate the resistance connected in parallel between the electrodes as is normally required for fixing the potential of the positive electrode.

The invention also provides a pressure wave generator apparatus including an electrical discharge circuit for providing an electrical discharge between two electrodes immersed in a liquid, wherein the electrical discharge circuit is as defined above and in particular comprises switch means connected in parallel between the electrodes, said switch means constituting a closed switch for low frequency current and constituting an open switch for high frequency current. The liquid may be water.

BRIEF DESCRIPTION OF THE DRAWINGS

Other objects, characteristics, and advantages of the invention appear clearly in the light of the following explanatory description made with reference to the accompanying drawings which show a presently preferred embodiment of the invention that is given purely by way of example and therefore does not limit the scope of the invention in any way. In the drawings:

FIG. 1 is a diagram of a truncated ellipsoidal reflector of the type described in Rieber's U.S. Pat. No. 2,559,227 together with an electrical discharge circuit between its electrodes;

FIG. 2 shows apparatus of the invention for generating pressure waves and comprising a truncated ellipsoidal reflector of the type shown in FIG. 1, but including a discharge circuit that is modified in accordance with the present invention.

MORE DETAILED DESCRIPTION

Figure 3:
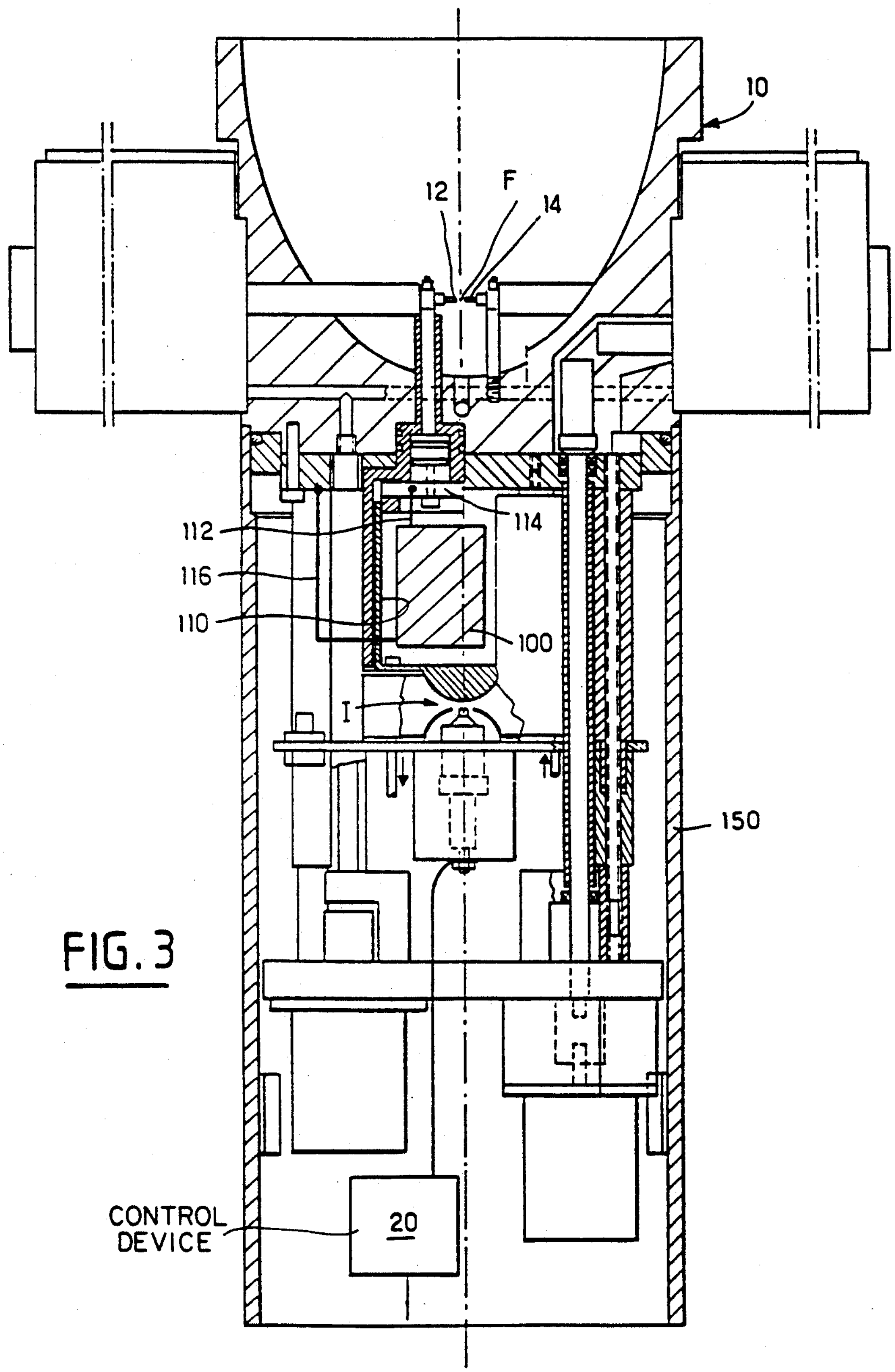
FIG. 3 is a vertical section view on a longitudinal plane of symmetry through the truncated ellipsoidal reflector having the structure shown in FIG. 2 of the Assignee's French patent application No. FR-A-2.646.744 which corresponds to PCT application serial no. WO 91/10227 published Jul. 11, 1991 in which the present modification of the discharge circuit of the invention has been incorporated.

FIG. 1 shows a truncated ellipsoidal reflector given a general reference 10 and of the type described in Rieber's U.S. Pat. No. 2,559,227, which is incorporated herein by reference, the reflector being provided with two diametrically opposite discharge electrodes 12 and 14 converging on the internal focus which is symbolized by reference F. The second focus of the ellipsoid is disposed outside the truncated ellipsoidal reflector 10, and a target to be destroyed is brought into coincidence with said second focus, as described at length in Rieber's U.S. patent. Naturally, in the event of lithotrity, the target may be constituted by a concretion, as in the event of osteotrity it may be constituted by bone.

The electrode 12, for example, is connected to Earth or circuit ground as shown in FIG. 1, and to one terminal of a capacitor C. The other electrode 14 is connected to the capacitor C via a switch device I, e.g. a gas discharger which is closed intermittently by a conventional control symbolically referenced 20. A high value resistance R, generally about 15 kΩ is connected in parallel with the capacitor C to fix the potential of the positive electrode for safety reasons. The capacitor C is subjected to a high tension of about 10,000 V to 20,000 V by a power source as described by Rieber, for example.

Normally the ellipsoidal reflector 10 is filled with a pressure wave transmission liquid, e.g. constituted by water, having non-negligible resistance to the passage of an electrical current. On average, the electrical resistance of normally ionized water expressed in terms of linear resistivity is about 1,500 Ω cm. When using an oil, given that oil is highly insulating, as described in Rieber's U.S. Pat. No. 2,559,227, then the linear resistivity value is about 3M Ω.cm to 5M Ω.cm.

When an electrical discharge takes place in the circuit of FIG. 1, it is necessary for R to be a resistance of high value, in general about 15 kΩ, to prevent it absorbing too much current. Unfortunately, this conflicts with detecting and correcting the positions of the electrodes where it is necessary to detect variations in resistance that are much less than 15 kΩ when the electrode is very close to the detector means, constituted by a feeler finger, for example, as represented in dashed lines 30 and as described in detail in U.S. Pat. No. 4,868,791 which is incorporated herein by reference. The detector means 30 is connected to a device 32 for measuring the electrical resistance between the feeler finger 36 and one or other of the electrodes 12 and 14 via appropriate electrical conductors such as 38 and 40. The measurement device 32 may include incorporated therein an item that signals any variation in resistance and that is also capable of transmitting information to control means 34 which may include a computer and which serve to send instructions to electrode advance means for advancing the electrodes 12 and 14, which means are designed to advance and withdraw the electrodes, preferably individually, independently, and by rotation, said electrode advance means being preferably as described in the prior documents of the Assignee, and in particular U.S. Pat. No. 4,730,614 which is incorporated herein by reference.

In the prior technique described in U.S. Pat. No. 4,868,791, a switch device 50 is provided for intermittently connecting the positive electrode such as 14 to ground M during detection and control of the positions of the electrodes. This switch is a component that is expensive, bulky, and difficult to implement since it must be capable of isolating voltages of 20 kV and it must be capable of being driven by an external source, e.g. a source of compressed air. Furthermore, like any other mechanical component, it suffers from problems of reliability over time and requires maintenance. It also needs to be protected by a fuse.

The present invention described below with reference to FIGS. 2 and 3 serves to solve this technical problem.

With reference to FIG. 2, a device constituting a discharge circuit of the invention is shown and is characterized in that it includes switch means 100 connected in parallel between the electrodes 12 and 14, said switch means 100 constituting a switch that is closed for low frequency current and a switch that is open for high frequency current. During an electrical discharge between the electrodes 12 and 14 a high frequency current is generated at a high voltage and for an extremely short period of time, i.e. during sudden changes of current. A low frequency current is generated by a DC current permanently applied to the electrodes as during detection and correction of the positions of the electrodes by means of a feeler finger such as 136 which is permanently fed with DC, with the opposite DC feed also being applied to one or other of the electrodes 12 and 14.

The switch means 100 preferably comprise at least one choke which serves to fix the low frequency potential of the positive electrode, which in this case is the electrode 14. This choke presents a pure inductance referenced $L_1$ in series with a pure resistance referenced $R_1$ and due to the cable used, which resistance is generally low in value.

The impedance Z of this choke has a modulus given by the following mathematical equation, well known to the person skilled in the art:

$$Z=\sqrt{(R_1^2+L_1^2\times w^2)}$$

in which $R_1$ is the pure resistance of the choke,
$L_1$ is the pure inductance of the choke,
and $w=2\pi f$ where $\pi$ equals about 3.14,
and f is the frequency of the current.

The invention is based on the fact that at low frequencies, f approaches zero, such that the impedance of the choke 100 is limited to its resistance, and it thus behaves like a pure resistance, whereas at high frequency, the inductive contribution to its impedance becomes large, thereby increasing its overall impedance. This property makes it possible to use the choke as a low value resistance at low frequency, thus constituting a closed circuit, and as an open circuit at high frequency, i.e. during a high voltage discharge delivered instantaneously between the electrodes as happens when generating a pressure wave as described in the above-mentioned documents, and in particular Rieber's U.S. Pat. No. 2,259,227.

In a particular variant embodiment of the invention, the choke 100 has an impedance that is very large relative to the impedance between the electrodes at the moment of discharge, with the choke impedance being preferably not less than 100 times, and better not less than 500 times, and better still not less than 1,000 times the impedance between the electrodes at the moment of discharge.

In a variant embodiment, the inductance $L_1$ of the choke 100 is selected so as to divert no more than 1%, and preferably no more than 1 per thousand of the discharge current between the electrodes.

In a practical application where the discharge voltage between the electrodes as delivered by the capacitor C is 20 kV, with the total discharge time being about 10 μs, the total inductance of the discharge circuit is about 100 nanohenries (nH), so a choke is used having a dielectric strength of 20 kV, a maximum resistance $R_1$ of about 50 Ω, and an inductance of about 20 mH.

In a particular variant embodiment, it is possible to dispose the previously used resistance R in parallel with the choke 100, as represented by dot-dashed lines in FIG. 2.

FIG. 3 shows one example of a location for the choke 100.

FIG. 3 is a vertical section view on a longitudinal plane of symmetry of the truncated ellipsoidal reflector 10 including the focal point and the electrodes 12 and 14 as shown, and having a structure as described with reference to FIG. 2 of French patent document FR-A-2.646.744 which corresponds to PCT application serial no. WO 91/10227 published Jul. 11, 1991 which is incorporated herein by reference.

In the structure shown in FIG. 2 of the Assignee's prior patent application, the switch device 1 is constituted by a gas discharger or "spark gap" well known to the person skilled in the art and having its operation under the control of a control device 20.

The choke 100 of the present invention is advantageously disposed in the space left empty inside the cylindrical conductive component 110 that is electrically connected to the positive electrode 12, as described in said prior document of the Assignee. The choke 100 of the present invention is electrically connected to the positive electrode 12, e.g. via an electrical conductor 112 connecting the choke 100 to a component 114 constituting a portion of the electrical conductors feeding the positive electrode 12, and to ground via a conductor 116 connecting the choke 100 directly or indirectly to the ground of the truncated ellipsoidal reflector 10.

This choke is thus indeed integrated in parallel with the circuit feeding the electrodes 12 and 14 and is well protected inside the protective tube 150 which has likewise been previously described.

The dimensions of this choke 100 may, for example, be the following: height 120 mm, diameter 56 mm.

The above-described discharge circuit between the electrodes 12 and 14, as shown in FIG. 2 and 3, forms an integral portion of the invention.

This discharge circuit makes it possible to detect and correct the position of the electrodes 12 and 14 in a manner similar to that described in U.S. Pat. No. 4,868,791, but with the following modifications.

Firstly, it is preferable to use a feeler finger 136 which is advanced parallel to the electrodes 12 and 14 and which includes a curved front portion 136a suitable for rotating into the path between the electrodes 12 and 14 by control means 135 provided for that purpose (see FIG. 2).

When detecting and correcting the positions of the electrodes, the feeler finger 136, 136a is permanently fed with low voltage DC, e.g. about 12 V delivered by the means 132. The method of detecting and correcting the position of an electrode is as follows:

Initially, the end 136a of the feeler finger 136 is disposed at the focal point F. Normally the electrodes 12 and 14 are situated on opposite sides of the feeler finger 136, as shown in FIG. 2.

Thereafter, one of the electrodes is advanced, e.g. the electrode 14 in this case, until it comes into contact with the end 136a of the feeler 136 disposed at the focal point F.

The presence of the electrode (in this case the electrode 14) at the focal point F is thus detected by the electrode making contact with the end 136a. This is done by measuring the resistance between the feeler finger 136 and the electrode (in this case 14), i.e. the resistance from the measuring device 132 into the electrical circuit comprising the conductor 137, the feeler finger 136–136a, the electrode 14, the choke 100, and the conductor 140.

When the electrode (in this case 14) comes into contact with the feeler finger 136, the resistance drops suddenly.

Once this sudden drop in resistance has been detected, then the electrode (in this case 14) is withdrawn through a predetermined distance d so that the electrode 14 takes up its proper position relative to the focus F.

The same procedure is applied to the other electrode or electrodes.

Because of the presence of the choke 100, it can be seen that the DC which is permanently applied to the feeler finger 136, 136a can pass freely through the choke 100 to reach the detection device 132 since the choke 100 constitutes a closed switch when passing a permanent DC, i.e. a low frequency.

In contrast, outside this period of detecting and monitoring the positions of the electrodes, the choke 100 constitutes an open switch which prevents the passage of a high frequency current as generated during the sudden discharge of the capacitor C when the switch I is closed.

It can be seen that the method and the apparatus of the invention can be used for detecting and correcting the positions of the electrodes accurately, simply, reliably, and cheaply.

This method and apparatus lend themselves well to full automation since, when there is no contact between the electrode being monitored and the feeler means 136, a digital value 0 may be taken, and when contact is achieved and the resistance drops suddenly, a digital value 1 may be taken, thereby enabling the data to be computer processed.

In addition, in the event of the control means 135 for the feeler means 136 breaking down, so that the feeler means 136 is not advanced, then the absence of any sudden drop in resistance being detected while an electrode is being advanced through a predetermined distance can be used to generate an alarm signal representative of misoperation.

In the event that the actuator does not return to its initial retracted position, this fault can be detected by the absence of contact between the feeler finger 136 and a contact which is actuated by the feeler finger 136 returning to its retracted position. It will be understood that such a safety precaution serves to verify that the feeler finger 136 has been retracted.

Initially, both electrodes are retracted far enough to ensure that the feeler finger 136 can take up a proper position on the path between the electrodes.

It will thus be understood that the invention extends to any means constituting technical equivalence of the means described and shown, and to various possible combinations thereof. In addition, the embodiment shown in FIGS. 2 and 3 constitutes an integral portion of the invention and thus of the present description.

In particular, the liquid in which the electrodes are immersed constitutes a discharge or coupling liquid enabling pressure waves to be generated when an electrical discharge takes place between the two immersed electrodes.

We claim:

1. An electrical discharge circuit for providing a discharge between two discharge electrodes immersed in a liquid comprising means for intermittently connecting a voltage source across said two electrodes, and a non-mechanical electronic switch connected in parallel with said electrodes, said switch presenting a low impedance approximating a short circuit condition for low frequency currents approximating a direct current, and said switch presenting a high impedance approximating an open circuit condition for higher frequencies including during discharge.

2. A circuit according to claim 1, wherein said switch comprises a choke.

3. A circuit according to claim 2, wherein the impedance of the choke is at least 100 times greater than the impedance between the electrodes at the moment of discharge.

4. A circuit according to claim 1, wherein a resistor having a high resistance is disposed in parallel with switch.

5. The circuit according to claim 1, further comprising means for detecting and correcting the position of at least one of said electrodes.

6. A circuit according to claim 2, wherein the impedance of the choke is at least 500 times greater than the impedance between the electrodes at the moment of discharge.

7. A circuit according to claim 2, wherein the impedance of the choke is at least 1,000 times greater than the impedance between the electrodes at the moment of discharge.

8. A method of detecting and correcting the position of at least one electrode of a plurality of electrodes in an electrode discharge device said electrodes being intended for disposition at a predetermined distance symmetrically about a focal point in three dimensional space at which an electrical discharge is to be generated (a) providing a non-mechanical electronic switch connected in parallel with said electrodes, said switch presenting a low impedance approximating a short circuit condition for low frequency currents approximating a direct current during detection, and said switch presenting a high impedance approximating an open circuit condition for higher frequencies, including during discharge;

(b) positioning a detector at a point, referred to as the detection point situated on the displacement path of the electrodes, which path includes said focal point, said detector detecting the presence of an electrode at a point in three dimensional space;

(c) applying a low frequency current approximating a direct current to said detector;

(d) advancing said at least one of the electrodes until it comes into contact with said detector while said detector is disposed at the detection point;

(e) detecting the presence of said at least one electrode at said detection point by a change in resistance in the circuit comprising said detector and said electrode when contact therebetween is established;

(f) withdrawing said at least one electrode to position said electrode at its predetermined distance about said focal point;

(g) performing steps (b)–(f) with at least another electrode in said plurality of electrodes; and (h) withdrawing the detector from said detection point.

9. Apparatus for detecting and correcting the position of at least one of a plurality of electrodes immersed in a liquid and for use in an electrode discharge device as in a pressure wave generator apparatus, said electrodes being intended for disposition at a predetermined distance symmetrically about a point in three dimensional space at which an electrical discharge is to be generated, comprising electrode advance means for advancing and retracting the electrodes; a detector means disposed at a predetermined point in three dimensional space referred to as the detection point, said point being situated on the displacement path of the electrodes, for detecting the presence of an electrode; means for moving said detector means relative to said displacement path for withdrawing said detector means from said detection point; means for measuring the electrical resistance between the detector means and an electrode, and means for indicating changes in said resistance, the apparatus including a non-mechanical electronic switch connected in parallel with said electrodes, said switch presenting a low impedance approximating a short circuit condition for low frequency currents approximating a direct current during detection, and said switch presenting a high impedance approximating an open circuit condition for higher frequencies including during discharge.

10. In an apparatus for generating pressure waves of the type comprising a pair of electrodes immersed in a liquid medium for generating an electrical discharge between said electrodes by intermittently connecting said electrodes to a voltage source, the improvement comprising a non-mechanical, electronic switch connected in parallel with said electrodes, said switch presenting a low impedance approximating a short circuit condition for low frequency currents approximating a direct current, and said switch presenting a high impedance approaching an open circuit condition for higher frequencies including during discharge.

11. Apparatus according to claim 10, wherein said apparatus is a lithotritor.

12. Apparatus according to claim 10, wherein said apparatus is a osteotritor.

13. Apparatus according to claim 10, wherein said apparatus is a means for treating tissue.

* * * * *